(12) United States Patent
Pumphrey

(10) Patent No.: US 10,636,105 B2
(45) Date of Patent: Apr. 28, 2020

(54) SYSTEM AND METHOD FOR SHIPPING PRODUCTS

(71) Applicant: ClearCorrect Operating, LLC, Round Rock, TX (US)

(72) Inventor: Jarrett Pumphrey, Round Rock, TX (US)

(73) Assignee: ClearCorrect Operating, LLC, Round Rock, TX (US)

( * ) Notice: Subject to any disclaimer, the term of this patent is extended or adjusted under 35 U.S.C. 154(b) by 328 days.

(21) Appl. No.: 15/616,682

(22) Filed: Jun. 7, 2017

(65) Prior Publication Data

US 2017/0365025 A1    Dec. 21, 2017

Related U.S. Application Data

(60) Provisional application No. 62/352,360, filed on Jun. 20, 2016.

(51) Int. Cl.
*G06Q 10/08* (2012.01)
*G06Q 30/06* (2012.01)
*G06Q 50/22* (2018.01)

(52) U.S. Cl.
CPC ......... *G06Q 50/22* (2013.01); *G06Q 10/0838* (2013.01); *G06Q 30/0635* (2013.01)

(58) Field of Classification Search
CPC ................................................. G06Q 10/0838
USPC ...................................................... 705/26.81
See application file for complete search history.

(56) References Cited

U.S. PATENT DOCUMENTS

2002/0178074 A1* 11/2002 Bloom ................... G06Q 10/08
                                                      705/26.81
2004/0153379 A1    8/2004 Joyce et al.
2005/0119786 A1    6/2005 Kadaba
2015/0081585 A1    3/2015 Kadaba

OTHER PUBLICATIONS

International Search Report dated Sep. 13, 2017 in International Application No. PCT/US2017/038281.
International Preliminary Report on Patentability dated Dec. 25, 2018 in International Application No. PCT/US2017/038281.
Extended European Search Report issued in EP Application No. 17816044.6 dated May 24, 2019.

* cited by examiner

*Primary Examiner* — Alexis M Casey
(74) *Attorney, Agent, or Firm* — Gardella Grace P.A.

(57) ABSTRACT

Systems and methods for real-time processing and linking of orders to enhance execution performance can be configured to receive an incoming order from a customer including product data, customer information, and shipping information; determine that the incoming order can be linked to an existing shipment bundle that has one or more orders assigned orders based on predetermined linking criteria; assign a bundle identification (ID) to the incoming order corresponding to the existing shipment bundle; and release the existing shipment bundle for shipment when one or more predetermined shipping criteria are met.

20 Claims, 4 Drawing Sheets

SYSTEM AND METHOD FOR SHIPPING PRODUCTS

CROSS-REFERENCE TO RELATED APPLICATIONS

This application claims the benefit of U.S. Provisional Application No. 62/352,360 filed Jun. 20, 2016.

This application relates generally to orthodontic dental appliances, and more particularly, to an improved system and method for shipping orders for dental appliances to dental professionals efficiently and resourcefully. To this end, the present disclosure provides a system and method for combining or aggregating multiple shipments or orders upon satisfying certain criteria.

BACKGROUND

An objective of orthodontics is to move a patient's teeth to positions where function and/or aesthetics are optimized. Dental appliances, such as metal-type braces, are applied to the patient's teeth by a dental/orthodontic professional for exerting a continual force on the teeth in order to gradually move them toward their intended positions. One alternative to metal-type braces is the use of progressive, removable aligners for gradually moving the teeth to their desired, final positions in a more abbreviated and comfortable manner for the patient.

In general, to fabricate a set of aligners, a patient will visit the dental/orthodontic professional who will obtain a dental impression of the initial position of the patient's teeth. Then, the dental/orthodontic professional sends a custom order to a medical device company to manufacture a set of aligners for the patient. Once the set of aligners is manufactured, the medical device company ships the set of aligners back to the dental/orthodontic professional for the patient's use. Often times, the medical device company may receive multiple orders from a single dental professional within a short period of time (e.g., the same day, or within a few days of each other). In turn, multiple sets of aligners are likely to be manufactured and ready for shipment to that single dental professional within a short period of time. Thus, the dental professional may receive multiple shipments on the same day which results in customer inconvenience, higher shipping costs, and extra wastage of materials.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

The present disclosure relates to a system and method for combining or aggregating multiple shipments of orthodontic aligner appliances to dental professionals, where, via processing circuitry, the system determines whether a scheduled shipment or order having an initial shipment date is aggregable or combinable with another scheduled shipment, updates the initial shipment date of the order to a new shipment date when the order is aggregable with another scheduled shipment, and links the order to an existing bundle having multiple scheduled shipments therein if the bundle has a shipment date and a delivery address matching the order.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

In the drawings, like reference numerals designate identical or corresponding parts throughout the several views.

DETAILED DESCRIPTION

Figure 1:
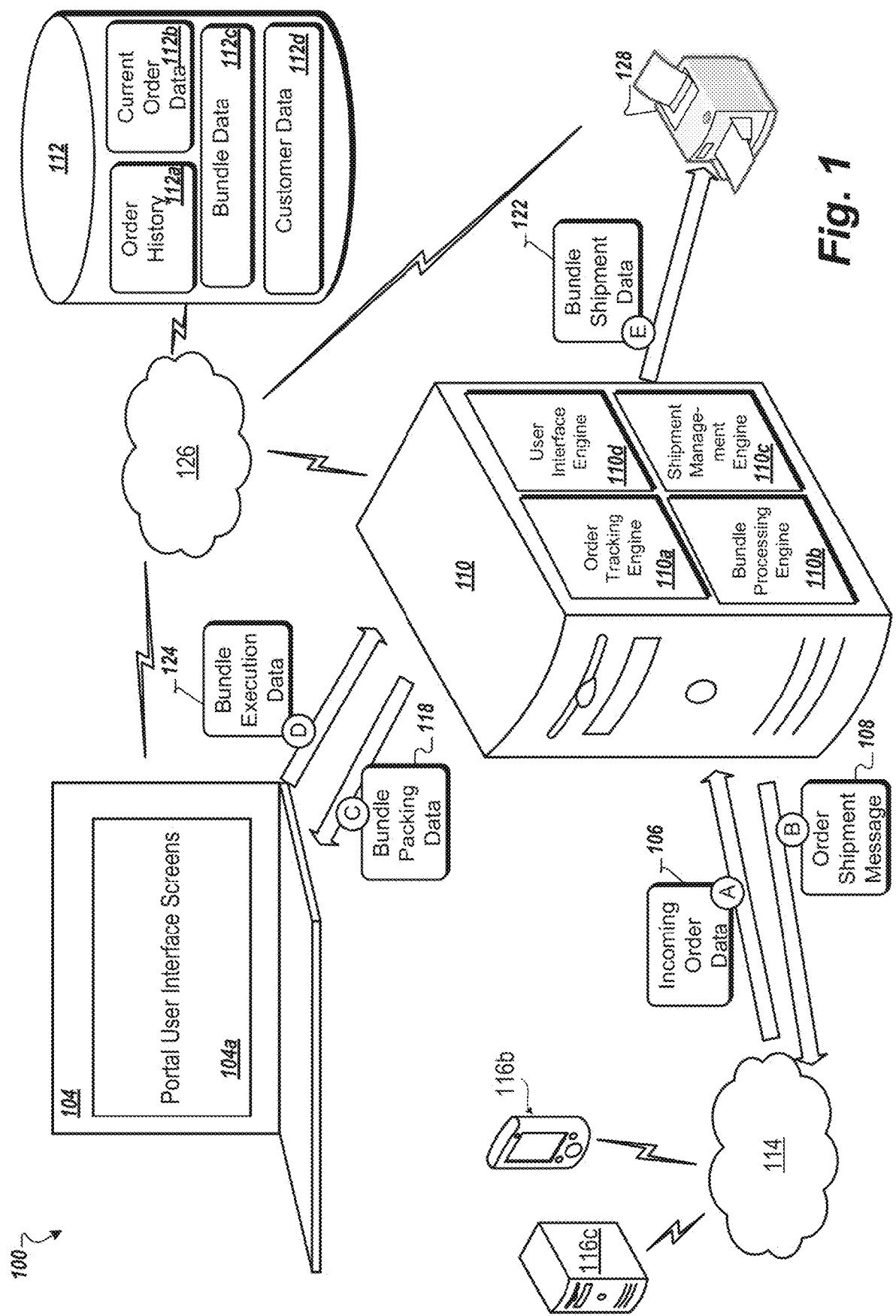
FIG. 1 is a schematic diagram of a system for combining or aggregating multiple shipments according to one example.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Referring now to the drawings, therein like reference numerals designate identical or corresponding parts throughout several views, the following description relates to a system and method for combining or aggregating multiple product shipment bundles into a single package or shipment if certain criteria are satisfied. For example, customers such as dental or orthodontic offices may place individual orders for orthodontic aligner appliances within a predetermined amount of time, such as a day, week, month, etc. Rather than mail each of the appliances as individual shipments to the customer, the system automatically links an incoming order to an existing order that is currently being processed based on shipping address or other customer identification data to reduce shipping costs and total number of packages shipped to the customer.

As an example, a medical device company may receive multiple orders for the fabrication of dental appliances, such as aligners, from dental professionals. Commonly, a dental professional may place a first order for a first set of aligners after an office visit of a first patient. Soon thereafter, a set of aligners is manufactured based on an initial tooth impression of the first patient and a desired, final tooth position. The dental professional may also place a second order for a second set of aligners after an office visit of a second patient within a short period of time (e.g., 1 hour, 2 hours, or 1 day). The first order has a first target ship date, and the second order has a second target ship date. Likely, the first and second set of aligners may be manufactured and ready for shipment the same day. Thus, the second target ship date of the second order may be modified to match the target ship date of the first order such that the dental professional receives both sets of shipments together, in a single shipment and on the same day. As such, the processes executed by a shipment bundling system described further herein result in shipping costs being reduced, which can cause increased customer satisfaction.

Herein, the following terms should be considered as similar, for the sake of explanation and/or discussion of the disclosure: shipment, box, container, parcel, package, pallet, and/or other terms used to describe an item or items that may be shipped, via any means, from one location to another (e.g., from a vendor to a customer).

FIG. 1 is a diagram of an example environment 100 for a shipment bundling system 110. The diagram illustrates interaction between one or more participants in the shipment bundling system 110, which receives orders for one or more products, tracks the orders through production, and links multiple orders into a shipment bundle based on customer, shipping data, etc. Shipment fill operators can interact with the shipment bundling system 110 through one or more web portal user interface screens 104a at a workstation 104 to view a current status of one or more orders for a particular customer or view the products assigned to a particular order or bundle. The workstation 104 may be a computer, laptop, or any other type of computing device at which the shipment fill operators can view current order, bundle, and shipment allocations.

Customers 116 can place orders at a customer computing device 116a or 116b that is transferred to the shipment bundling system 110 via network 114. In some implementations, the customers 116 interact with the shipment bundling system 110 via one or more user interface (UI) screens. For example, the customers 116 can submit orders at an order submission UI screen that allows the customers to upload impression or dental scan data along with customer identification, shipment, or payment information. The customers 116 can also view previous orders at an order history UI screen where the shipment bundling system 110 outputs order history data 112a from data repository 112. The customers 116 can also update customer data 112d stored in the data repository 112d at a customer data UI screen. The customer data 112d can include customer identification information such as a customer ID, shipping address, billing information, type of practice, or any other identifying features of the customers 116. The shipment bundling system 110 can also output the incoming order data 106 to an order status UI screen that can be viewed at the customer computing devices 116a or 116b that provides a real-time status of the products ordered by the customer 116.

References to bundles throughout the disclosure refer to a shipment that is configured to be sent to a customer 116 that includes one or more products. For example, if the customer 116 is a particular dentist who submits four orders for four custom orthodontic aligners throughout the course of a day, a shipment bundle can include the four orthodontic aligners that are packaged into a single box and shipped to the customer 116. In some implementations, a shipment bundle may have a maximum number of allowed products, and when the shipment bundle for the customer 116 reaches the maximum number of allowed products, then the shipment bundle is sent to the customer 116, and a new shipment bundle can be created. Shipments and bundles can be referred to interchangeably throughout the disclosure.

The shipment bundling system 110 communicates with customers 116, such as dentists, orthodontists, or any other type of customer, via a customer network 114. As such, a particular order may be submitted directly to the shipment bundling system 110 via the customer computing device 116a or 116b. The customer network 114, depending upon the deployment configuration of the shipment bundling system 110, may include the Internet, one or more intranets, local area networks (LANs), Wide Area Networks (WANs), and/or Metropolitan Area Networks (MANs). Further, although the customer devices 116 are illustrated as communicating with the customer network 114 through wireless connections, depending upon the deployment configuration, some customer devices 116 may communicate with the customer network via a wired or cabled connection. Additionally, in some embodiments, at least a portion of the networking configuration of the customer network 114 may be shared with a backend network 126 that connects the shipment bundling system 110 to the work station 104, data repository 112, at least one printer 128, and other peripheral devices such as a product scanner that may be configured to scan a bar code of a product that is placed in a box for shipping. Based on the deployment configuration, backend network 126 can also include communicate through one or more types of wireless or wired connections.

The shipment bundling system 110 may include one or more servers with one or more engines or modules that perform processes associated with receiving orders from the customers 116, tracking the orders as the orders are manufactured or accessed from an inventory warehouse, processing order bundles that include one or more products being sent to a particular customer 116, linking incoming orders to existing shipment bundles, and managing shipment of the bundles to the customers. References to the engines or modules throughout the disclosure are meant to refer to software processes executed by circuitry of one or more processing circuits, which can also be referred to interchangeably as processing circuitry. The processes performed by the engines of the shipment bundling system 110 can be executed in real-time in order to provide an immediate response to a system input. In addition, the processes can also be performed automatically in response to a process trigger that can include the reception of data from a data repository, a participant, or another processing engine. Also, the processes performed by the engines of the shipment bundling system 110 contribute to a reduction in a total number of shipments sent to the customer 116 by automatically generating shipment bundles of multiple orders being shipped to the same customer 116.

In one example, an order tracking engine 110a includes one or more processes associated with receiving incoming order data 106 from customers 106 in the shipment bundling environment 100, tracking a current step in the production process for the products in the order, and outputting an order shipment message 108 to the customers 116 via the network 114 when an order has been released for shipment. For example, the order tracking engine 110a receives the incoming order data 106 from the customer 116 that can include dimensional specifications associated with the product from either a mold impression or an oral scan. The incoming order data 106 may also include, but is not limited to, a customer ID, an order ID, a shipping address, item(s) ordered, associated quantities of ordered items, method of shipment, a ship-by-date, and the like. The customer ID may be a unique number that is associated with the customer. The order ID is a unique number that can be generated by the order tracking engine 110a when the incoming order data 106 is received. In some implementations, for existing customers that have had prior interactions with the shipment bundling system 110, the incoming order data 106 includes only the customer ID, and the order tracking engine 110a accesses a customer name and shipping address from the customer data 112d stored in data repository 112 as associates the customer data 112d with the incoming order data 106.

The order tracking engine 110a maintains a current status of the products in an order starting from when the incoming order data 106 is received until the order is released for shipping to the customer 116. For example, current statuses for the products can include "ORDER RECEIVED," "ORDER PROCESSING," "MANUFACTURING," "QUALITY CONTROL (QC) INSPECTION," "QC REJECTION," "READY TO SHIP," "IN SHIPPING BOX," or "PROCESSED FOR SHIPMENT." In some implementations, the order tracking engine 110a determines an order shipment date for the order associated with the incoming order data 106 based on the number of products in the order and an amount of manufacturing time associated with the products in the order. The order tracking engine 110a stores the incoming order data 106, the assigned shipping date, current status, and any data relevant to the order in the data repository 112 as current order data 112b.

The shipment bundling system 110 also includes a bundle processing engine 110b that links incoming orders with existing bundles based on predetermined linking criteria. For example, the predetermined linking criteria can include the customer name, address, assigned shipping date, shipping carrier, or maximum number of allowed products that can be assigned to the bundle. When one or more products from multiple orders are scheduled to ship the same day to the same address, the order linking engine 110b may create a bundle or link the one or more products to an existing bundle. In some implementations, the order linking engine 110b links the one or more products of the order to the existing bundle if a difference between a shipping date for the existing bundle and the incoming order is less than a predetermined number of days. In one example, the predetermined number of days is three. If the shipping date for the incoming order falls after the shipping date for the existing bundle, then the bundle processing engine 110b updates the shipping date for the existing bundle to correspond to the shipping date for the incoming order. For example, an incoming order may have a shipping date of May 25 assigned by the order tracking engine 110a. When the bundle processing engine 110b links the incoming order to an existing bundle being sent to the same customer as the incoming order that has a shipping date of May 24, the bundle processing engine 110b also updates the shipping date for the existing bundle to May 25 along with the current order data 112b for any other orders previously assigned to the existing bundle.

When a new bundle is created for the incoming order, the bundle processing engine 110b generates a bundle identification (ID) for the bundle that is unique and independent from the order ID for the orders assigned to the bundle. The bundle processing engine 110b stores the bundle ID, identification data for the products from the assigned orders, assigned order IDs for the bundle, and the bundle shipping date as bundle data 112c in the data repository 112. In some implementations, each product that is ordered as an associated order ID and bundle ID.

In some implementations, a bundle may include one assigned order, but other bundles may have multiple assigned orders. The bundle processing engine 110b determines how many of the assigned orders have been added to a shipping box for the bundle and transfers control of the bundle to the shipment management engine 110c when the shipping box has been filled with a maximum number of products from the assigned orders or a packing time has been reached. In some implementations, the packing time is a latest time that the shipment fill operators can begin packing the shipment boxes to ensure that the shipment boxes are ready by a pick-up time of a shipping carrier. In one example, the packing time is thirty minutes prior to the pick-up time of a shipping carrier. In some implementations, the bundle processing engine 110b can modify the packing time based on the number of bundles to be shipped within a day or other predetermined amount of time is greater than a predetermined threshold. For example, if the number of bundles to be shipped in a day is greater than the predetermined threshold, then the bundle processing engine 110b may modify the packing time to be one hour prior to the pick-up time for the shipping carrier.

The shipment fill operators may be individuals or automated devices that can interact with the bundle processing engine 110b via the workstation 104 at one or more portal user interface (UI) screens 104a. The bundle processing engine 110b can output bundle shipment data 118 at a bundle processing UI screen, which includes information associated with the orders assigned to a particular bundle along with customer identification information for the bundle. As the shipment fill operators place the products into the box associated with the bundle, product bar codes or labels are scanned with a product scanner that indicates to the bundle processing engine 110b that the product has been added to the box for the particular bundle, which can be referred to as bundle execution data 124. When the bundle processing engine 110b receives the bundle execution data 124, the bundle processing engine 110b updates the current order data 112b for the scanned products of the orders assigned to the bundle to indicate that the products have been packed for shipment. The processes performed by the bundle linking engine 110b are performed automatically and are transparent to the shipment fill operators and any other personnel interacting with the shipment bundling system 110. For example, the bundle execution data 124 viewed by the shipment fill operators on the portal UI screen may only include the products associated with the bundle without any indication of which order the products belong to.

The shipment bundling system 110 also includes a shipment management engine 110c that controls processes associated with releasing the packaged bundles for shipment. In some implementations, the bundle processing engine 110b transfers control of the bundle to the shipment management engine 110c when the shipping box for a particular bundle has been filled with the maximum number of allowed products from the previously assigned orders or the packing time has been reached. In response to receiving a trigger or message from the bundle processing engine 110b indicating that a particular bundle has been filled with the products from the assigned orders, the shipment management engine 110c outputs bundle shipment data 122 to printer 128, which can include shipping label data and bundle manifest data. The printer 128 outputs the bundle manifest, which can be added to the shipping box for the bundle. The printer 128 also outputs the shipping label that is applied to the bundle. Once the shipment management engine 110c outputs the bundle shipment data 122 to the printer 128, the shipment management engine 110c updates the status of the current order data 112b to reflect that the status of the orders in the bundle is "PROCESSED FOR SHIPMENT." In some implementations, the shipping labels are scanned by the scanning devices connected to the shipment bundling system 110 via the network 126 as the boxes for the bundles are picked up by the shipping carrier, and shipment management engine 110c updates the current order data 112b to indicate that the current status of the orders in the bundle is "SHIPPED."

The shipment bundling system 110 also includes a user interface engine 110d that manages the information output to and received from the UI screens associated with the shipment bundling system 110. For example, the user interface engine 110d outputs one or more web portal user interface screens 104a at the workstation 104 so that shipment fill operators can view a current status of one or more orders for a particular customer or view the products assigned to a particular bundle. The user interface engine 110d can also control the one or more customer user interface screens where the customers 116 can submit orders at an order submission UI screen that allows the customers to upload impression or dental scan data along with customer identification, shipment, or payment information. The user interface engine 110d can also control the order history UI screen where the customers 116 can view previous orders, a customer data UI screen where the customers 116 can update customer data 112d stored in the data repository 112d, and an order status UI screen where a real-time current order status can be viewed at the customer computing devices 116a or 116b.

The shipment bundling environment 100 also includes the data repository 112 that stores the order history data 12a, current order data 112b, bundle data 12c, and customer data 112d. In some implementations, the data repository 112 is a relational database that can store multiple data files in any format that is readable by the shipment bundling system 110. In some examples, one or more servers of the shipment bundling system 110 can be integrated with the data repository 112 to form an open-source relational database management system (RDBMS), such as a MICROSOFT MySQL RDBMS. In some implementations, the order history data 112a, current order data 112b, bundle data 112c, and customer data 112d are stored in a tabular format that can be accessed, modified, or created by the shipment bundling system 110 during the processes performed by the various engines of the shipment bundling system 110. For example, when a new bundle is created, the bundle processing engine 110b can generate the bundle ID that is stored in at least one file of the bundle data 112c along with the products of the orders assigned to the bundle. Also, as the status of the order is modified through the course of order processing and shipment, the order tracking engine 110a updates the current status of the order in the current order data 112b.

Figure 2:
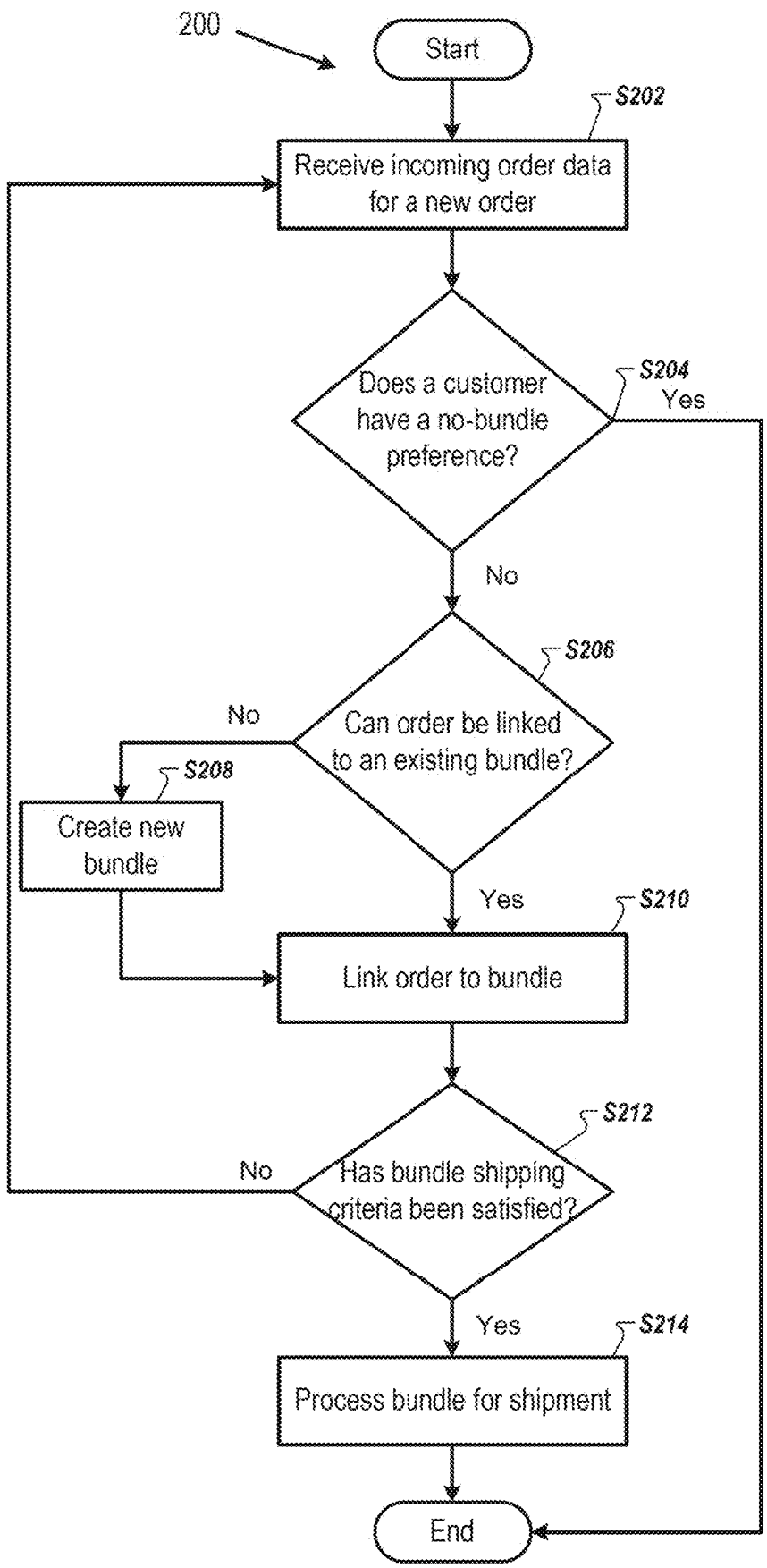
FIG. 2 is an exemplary flowchart of an order processing and linking process according to one example.

FIG. 2 is an exemplary flowchart of an order processing and linking process 200. In some implementations, steps of the order processing and linking process 200 are executed as software instructions by the processing circuitry of engines 110a, 110b, 110c, and 110d of the shipment bundling system 110 of FIG. 1. The order processing and linking process 200 may operate in real-time to process orders, link orders to bundles, and process the bundles for shipment. In addition, the order processing and linking process 200 may operate automatically to process the incoming order data 106 received from the customers 116, update the current status of the current order data 112b in the database, etc.

At step S202, the order tracking engine 110a receives the incoming order data 106 from the customer 116 that can include dimensional specifications associated with the product from either a mold impression or an oral scan. The incoming order data 106 may also include, but is not limited to, a customer ID, an order ID, a shipping address, item(s) ordered, associated quantities of ordered items, method of shipment, a ship-by-date, and the like. The customer ID may be a unique number that is associated with the customer. The order ID is a unique number that can be generated by the order tracking engine 110a when the incoming order data 106 is received. In some implementations, for existing customers that have had prior interactions with the shipment bundling system 110, the incoming order data 106 includes only the customer ID, and the order tracking engine 110a accesses a customer name and shipping address from the customer data 112d stored in data repository 112 as associates the customer data 112d with the incoming order data 106.

The order tracking engine 110a maintains a current status of the products in an order starting from when the incoming order data 106 is received until the order is released for shipping to the customer 116. For example, current statuses for the products can include "ORDER RECEIVED," "ORDER PROCESSING," "ORDER IN MANUFACTURE," "ORDER IN QUALITY CONTROL (QC)," "QC REJECTION," "READY TO SHIP," "IN SHIPPING BOX," or "PROCESSED FOR SHIPMENT." In some implementations, the order tracking engine 110a assigns a scheduled order shipment date for the order associated with the incoming order data 106 based on the number of products in the order and an amount of manufacturing time associated with the products in the order. The order tracking engine 110a stores the incoming order data 106, the assigned shipping date, current status, and any data relevant to the order in the data repository 112 as current order data 112b.

Then, at step S204, the order tracking engine 110a determines whether the customer 110a submitting the order associated with the incoming order data 106 has a no-bundle preference, which means that the customer 116 prefers to have each order shipped individually. The no-bundle preference can be accessed from the customer data 112d in the data repository 112 or can be included as part of the incoming order data 106. If it is determined that the customer 116 has a no-bundle preference, resulting in a "yes" at step S202, then the process is terminated. Otherwise, if the customer 116 does not have a no-bundle preference, resulting in a "no" at step S204, then step S206 is performed.

At step S206, once the incoming order data 106 has been processed by the order tracking engine 110a, the bundle processing engine 110b determines whether the order can be linked to an existing bundle based on predetermined linking criteria that can include the customer, shipping address, shipping date, preferred shipping carrier, number of product vacancies for the bundle, etc. In some implementations, the number of product vacancies for the bundle corresponds to the maximum number of allowed products in a bundle minus a number of currently assigned products. For example, the order can be linked to the bundle if the, the number of products in the incoming order is less than or equal to the number of product vacancies. In addition, the order can be linked to an existing bundle if the incoming order and the existing bundle are associated with the same customer and a difference between a shipping date for the existing bundle and the incoming order is less than a predetermined number of days. If it is determined that incoming order can be linked to an existing bundle based on the predetermined linking criteria, resulting in a "yes" at step S206, then step S210 is performed. Otherwise, if it is determined that the order cannot be linked to the existing bundle based on the predetermined linking criteria, resulting in a "no" at step S206, then step S208 is performed.

At step S208, if it is determined at step S206 that the incoming order does not meet the predetermined bundling criteria with any existing bundle, then the bundle processing engine 110b creates a new bundle for the incoming order. When a new bundle is created for the incoming order, the bundle processing engine 110b generates a bundle identification (ID) for the bundle that is unique and independent from the order ID for the orders assigned to the bundle. The bundle processing engine 110b stores the bundle ID, identification data for the products from the assigned orders, assigned order IDs for the bundle, and the bundle shipping date as bundle data 112c in the data repository 112. In some implementations, each product that is ordered has an associated order ID and bundle ID.

At step S210, if it is determined at step S206 that the incoming order meets the predetermined bundling criteria an existing bundle, then the bundle processing engine 110b links the incoming order to the existing bundle by assigning a bundle ID to the incoming order that corresponds to the bundle ID of the existing bundle. Also, if the shipping date for the incoming order and the shipping date for the existing bundle are not the same, the bundle processing engine 110b updates either the bundle shipping date or the order shipping date. For example, if the order shipping date falls on a date that is prior to the bundle shipping date, then the order shipping date is modified to correspond to the bundle shipping date. Likewise, if the shipping date for the incoming order falls after the shipping date for the existing bundle, then the bundle processing engine 110b updates the shipping date for the existing bundle to correspond to the shipping date for the incoming order. For example, an incoming order may have a shipping date of May 25 assigned by the order tracking engine 110a. When the bundle processing engine 110b links the incoming order to an existing bundle being sent to the same customer as the incoming order that has a shipping date of May 24, the bundle processing engine 110b also updates the shipping date for the existing bundle to May 25 along with the current order data 112b for any other orders previously assigned to the existing bundle.

At step S212, the bundle processing engine 110b determines whether one or more bundle shipping criteria have been satisfied. For example, the bundle shipping criteria can include situations where the shipping box associated with a bundle has been filled with the maximum number of allowed products from the previously assigned orders or a packing time has been reached. In some implementations, the packing time is a latest time that the shipment fill operators can begin packing the shipment boxes to ensure that the shipment boxes are ready by a pick-up time of a shipping carrier. In one example, the packing time is thirty minutes prior to the pick-up time of a shipping carrier. In some implementations, the bundle processing engine 110b can modify the packing time based on the number of bundles to be shipped within a day or other predetermined amount of time is greater than a predetermined threshold. For example, if the number of bundles to be shipped in a day is greater than the predetermined threshold, then the bundle processing engine 110b may modify the packing time to be one hour prior to the pick-up time for the shipping carrier. If the bundle processing engine determines that one or more of the bundle shipping criteria have been met for a bundle being processed, resulting in a "yes" at step S212, then the bundle processing engine 110b passes control for the bundle to the shipment management engine 110c and step S214 is performed. Otherwise, if the bundle processing engine determines that one or more of the bundle shipping criteria have not been met for a bundle being processed, resulting in a "no" at step S212, then the process returns to step S202 to process new incoming orders.

At step S214, in response to receiving a trigger or message from the bundle processing engine 110b indicating that a particular bundle has been filled with the products from the assigned orders, the shipment management engine 110c outputs bundle shipment data 122 to printer 128, which can include shipping label data and bundle manifest data. The printer 128 outputs the bundle manifest, which can be added to the shipping box for the bundle. The printer 128 also outputs the shipping label that is applied to the bundle. Once the shipment management engine 110c outputs the bundle shipment data 122 to the printer 128, the shipment management engine 110c updates the status of the current order data 112b to reflect that the status of the orders in the bundle is "PROCESSED FOR SHIPMENT." In some implementations, the shipping labels are scanned by the scanning devices connected to the shipment bundling system 110 via the network 126 as the boxes for the bundles are picked up by the shipping carrier, and shipment management engine 110c updates the current order data 112b to indicate that the current status of the orders in the bundle is "SHIPPED."

Figure 3:
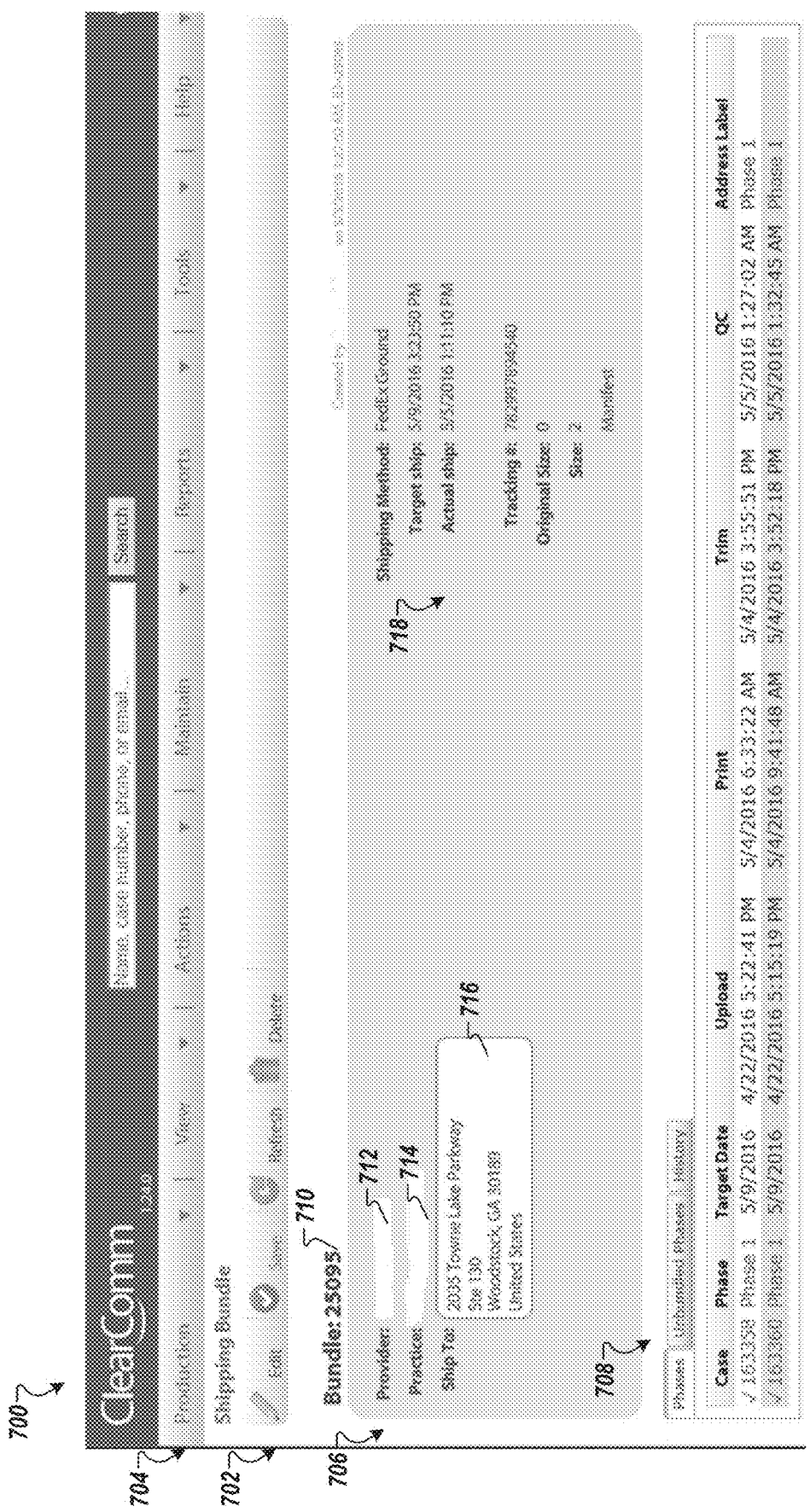
FIG. 3 is a schematic that shows a graphical user interface according to one example.

FIG. 3 is a schematic that shows a user interface (UI) screen 300 according to one example. The UI screen 300 may be part of a website, web portal, personal computer application, or mobile device application configured to allow a user to interact with the shipment bundling system 110. For example, the UI screen 300 may be one of the web portal user interface screens 104a viewed at the workstation 104 that allows the shipment fill operators to view a current status of one or more orders for a particular customer or view the products assigned to a particular order or bundle. The UI screen 300 may include a "shipping bundle" pane 302, a "navigation" pane 304, a "bundle information" pane 306, and a "status" pane 308.

The "shipping bundle" pane 302 presents the user with four navigational controls for editing, storing, refreshing, and deleting a shipment bundle.

The "navigation" pane 304 presents the user with a plurality of navigational controls for navigating to various stages of the production of items (e.g., the set of aligners).

The "bundle information" pane 306 presents the user with information about the bundle. A first field 310 represents the bundle's unique ID number. A second field 312 is for a recipient's name. A third field 314 is for a practice's name. A fourth field 316 shows address information. The first field 310, the second field 312, the third field 314, and the fourth field 316 may be automatically populated by the user interface engine 110d based on the current order information 106 stored in the data repository 112. A fifth field 318 represents shipment information. The fifth field 718 also includes a "ship" control (not shown). Upon activation of the "ship" control, the shipping label is created and the status of the bundle is updated to "shipped". Once the shipment is released or shipped, the "ship" control is "hidden" and the fifth field 318 shows shipping information that is either populated automatically or by an operator, as shown in FIG. 3.

The "status" pane 308 presents the user with navigational controls for displaying information about the cases and phases of the cases that are included in the bundle. Further, the UI screen 300 shows information related to the identity of the operator and the various stages of manufacturing, such as the date and time when each stage of the manufacturing is completed.

Figure 4:
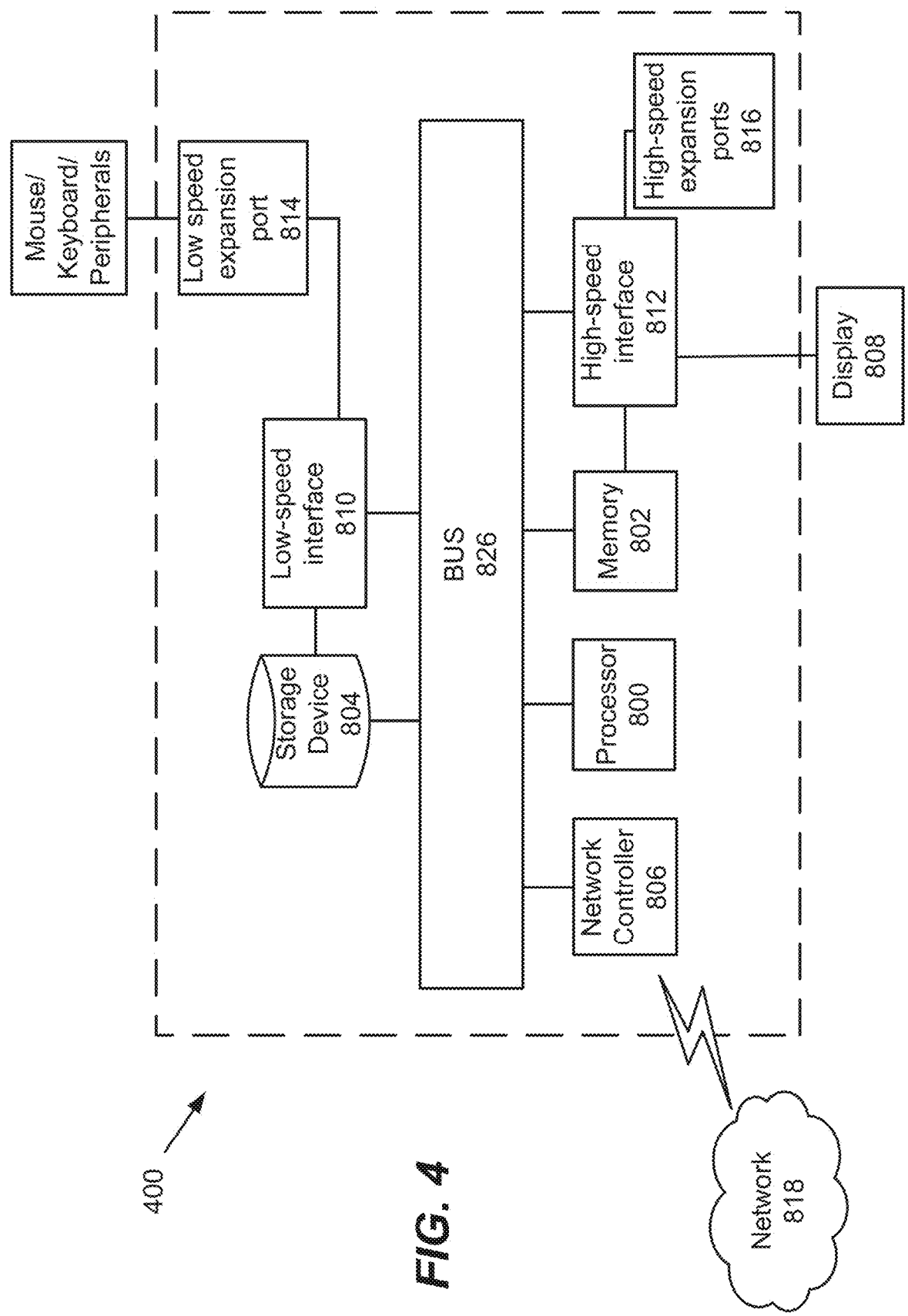
FIG. 4 illustrates a block diagram of an exemplary computing device according to one example.

FIG. 4 shows an example of a computing device 400, such as the shipment bundling system 110 that can be used to implement the techniques described in this disclosure. In some implementations, the computing device 100 can represent one or more of the engines of the shipment bundling system 110. The computing device 100 is intended to represent various forms of digital hardware, such as laptops, desktops, workstations, personal digital assistants, servers, blade servers, mainframes, and other appropriate computers. The components shown here, their connections and relationships, and their functions, are meant to be examples only, and are not meant to be limiting.

The computing device 400 includes a processor 400, a memory 402, a storage device 404, a high-speed interface 412 connecting to the memory 402 and multiple high-speed expansion ports 416, and a low-speed interface 410 connecting to a low-speed expansion port 414 and the storage device 404. Each of the processor 400, the memory 402, the storage device 404, the high-speed interface 412, the high-speed expansion ports 416, and the low-speed interface 410, are interconnected using various busses, such as communication bus 426, and may be mounted on a common motherboard or in other manners as appropriate.

The processor 400 can process instructions for execution within the computing device 400, including instructions stored in the memory 402 or on the storage device 404 to display graphical information for a GUI on an external input/output device, such as a display 408 coupled to the high-speed interface 412. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). The memory 402 stores information within the computing device. In some implementations, the memory 402 is a volatile memory unit or units. In some implementations, the memory 402 is a non-volatile memory unit or units. The memory 402 may also be another form of computer-readable medium, such as a magnetic or optical disk.

The storage device 404 is capable of providing mass storage for the computing device 400. In some implementations, the storage device 404 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 400), perform one or more methods, such as those described above. The instructions can also be stored by one or more storage devices such as computer- or machine-readable mediums (for example, the memory 402, the storage device 404, or memory on the processor 400).

The high-speed interface 412 manages bandwidth-intensive operations for the computing device 400, while the low-speed interface 410 manages lower bandwidth-intensive operations. Such allocation of functions is an example only. In some implementations, the high-speed interface 412 is coupled to the memory 402, the display 408 (e.g., through a graphics processor or accelerator), and to the high-speed expansion ports 416, which may accept various expansion cards (not shown). In the implementation, the low-speed interface 410 is coupled to the storage device 804 and the low-speed expansion port 414. The low-speed expansion port 414, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 also includes a network controller 406, such as an Intel Ethernet PRO network interface card from Intel Corporation of America, for interfacing with a network 418. As can be appreciated, the network 418 can represent the customer network 114 or the backend network 126 and can be a public network, such as the Internet, or a private network such as an LAN or WAN network, or any combination thereof and can also include PSTN or ISDN sub-networks. The network 818 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

Although the computing device of FIG. 8 is described as having a storage medium device 804, the claimed advancements are not limited by the form of the computer-readable media on which the instructions of the inventive process are stored. For example, the instructions may be stored on CDs. DVDs, in FLASH memory, RAM, ROM, PROM, EPROM, EEPROM, hard disk or any other information processing device with which the computing device communicates.

In other alternate embodiments, processing features according to the present disclosure may be implemented and commercialized as hardware, a software solution, or a combination thereof. Moreover, instructions corresponding to the order processing and linking process 200 in accordance with the present disclosure could be stored in a portable drive such as a USB Flash drive that hosts a secure process.

Computer programs (also known as programs, software, software applications or code) associated with the processes described herein, such as the order processing and linking process 200, include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, an implementation may be performed on modules or hardware not identical to those described. Accordingly, other implementations are within the scope that may be claimed.

The implementations of the shipment bundling system 110 within the shipment bundling environment 100 described herein provide advantages over existing systems that separately ship individual orders to customers that include but are not limited to providing automatic and real-time linking of orders that are being shipped to the same customer within a predetermined number of days, which reduces a total number of shipments that are sent out on a daily basis. Also, order linking processes are automatically executed in a manner that is transparent to the shipment fill operators and any other personnel interacting with the shipment bundling system 110, by only releasing a particular bundle for packing and shipment when the bundle shipment criteria have been met so that the shipment fill operators may be unaware whether the products in a particular bundle are associated with one order or multiple orders.

Accordingly, Applicant(s) intend(s) to embrace all such alternatives, modifications, equivalents, and variations that are within the spirit and scope of the disclosed subject matter.

The invention claimed is:

1. A system comprising:
  processing circuitry executing upon at least one computing device;
  a non-transitory data storage region for storing data associated with a plurality of orders for customized products placed by a plurality of customers; and
  a non-transitory computer readable medium, coupled to the processing circuitry, storing machine-executable instructions operable when executed on the processing circuitry to cause the processing circuitry to:
    receive, via a network from a computing system associated with a customer of the plurality of customers, an incoming order for fabricating one or more customized products,
      wherein the incoming order includes customized product fabrication data for each of the one or more customized products, customer information, and shipping information, and
      wherein the incoming order is one of a plurality of incoming orders of the plurality of orders received from the customer,
    determine, based on the customized fabrication data, an amount of fabrication time for each of the one or more customized products in the incoming order,
    determine, based on the amount of fabrication time for each of the one or more customized products, an order shipment date for the incoming order,
    in response to determining one or more predetermined linking criteria are met, the predetermined linking criteria including i) the order shipment date is within a predetermined number of days of a bundle shipment date for a shipment bundle containing one or more other orders of the plurality of incoming orders of the customer, and ii) a number of product vacancies in the shipment bundle is greater than a number of products in the incoming order, link, within the non-transitory data storage region, the incoming order to the shipment bundle, wherein
      the shipment bundle is one of a plurality of shipment bundles, each shipment bundle including one or more orders of the plurality of orders, and
      linking the incoming order to the shipment bundle includes assigning a bundle identification (ID) to the incoming order corresponding to the shipment bundle, and
    after linking the incoming order to the shipment bundle and in response to determining that one or more predetermined shipping criteria are met, generate, for review by a user, a bundle shipment manifest for use in preparing the shipment bundle for shipping, wherein
      the bundle shipment manifest is generated from a portion of the data associated with each of the customized products assigned to the bundle ID, and
      the bundle shipment manifest lacks reference to the respective order of the plurality of incoming orders associated with each of the customized products.

2. The system of claim 1, wherein the instructions, when executed by the processing circuitry, further cause the processing circuitry to:
  assign, responsive to receiving the incoming order, an order identification (ID) distinguishing the incoming order from other orders.

3. The system of claim 2, wherein assigning the bundle ID comprises determining the bundle ID that is unique and independent from the order ID.

4. The system of claim 1, the instructions, when executed by the processing circuitry, further cause the processing circuitry to:
  track, in real-time responsive to receiving the incoming order, a current status of the incoming order until the corresponding linked shipment bundle is released for shipment, wherein the current status includes a current step in a fabrication process for the incoming order.

5. The system of claim 1, wherein linking the incoming order to the shipment bundle comprises identifying a correspondence between at least one of customer name, address, or assigned shipping date of the incoming order and at least one of customer name, address, or assigned shipping date of the incoming order.

6. The system of claim 1, wherein the predetermined number of days between the order shipment date and the bundle shipment date for a shipment bundle is three days.

7. The system of claim 1, the instructions, when executed by the processing circuitry, further cause the processing circuitry to:
modify, responsive to assigning the bundle ID to the incoming order corresponding to the shipment bundle, the shipment date for the shipment bundle to correspond to the shipment date for the incoming order when the shipment date for the incoming order is after the shipment date for the for the shipment bundle.

8. The system of claim 1, the instructions, when executed by the processing circuitry, further cause the processing circuitry to:
modify, responsive to assigning the bundle ID to the incoming order corresponding to the shipment bundle, the shipment date for the incoming order to correspond to the shipment date for the shipment bundle when the shipment date for the shipment bundle is after the shipment date for the incoming order.

9. The system of claim 1, wherein the number of product vacancies in the shipment bundle corresponds to a maximum number of allowed products in the shipment bundle minus a number of currently assigned products.

10. The system of claim 1, wherein the instructions, when executed by the processing circuitry, further cause the processing circuitry to:
generate, in response to determining that the one or more predetermined linking criteria for linking the incoming order to the shipment bundle are not met, a new bundle ID associated with a new shipment bundle.

11. The system of claim 10, wherein generating the new bundle ID associated with the new shipment bundle comprises assigning the new bundle ID to the incoming order.

12. The system of claim 1, wherein determining that the one or more predetermined shipping criteria are met comprises determining that a number of products assigned to the shipment bundle corresponds to a maximum number of allowed products for each of the plurality of shipment bundles.

13. The system of claim 1, wherein determining that the one or more predetermined shipping criteria are met comprises determining that a current time corresponds to a packing time for one or more of the plurality of shipment bundles.

14. The system of claim 13, wherein the packing time is based on a package pick-up time of a shipping carrier.

15. The system of claim 13, wherein the instructions, when executed by the processing circuitry, further cause the processing circuitry to:
modify, responsive to determining that the one or more of the plurality of shipment bundles to be packed is greater than a threshold, the packing time for the one or more of the plurality of shipment bundles.

16. The system of claim 1, wherein generating the bundle shipment manifest comprises transmitting, to a printer communicatively coupled to the processing circuitry via the network, the bundle shipment manifest.

17. A non-transitory computer readable medium having instructions stored thereon, wherein the instructions, when executed by the processor, cause the processor to:
receive, via a network from a computing system associated with a customer of a plurality of customers, an incoming order for fabricating one or more customized products,
wherein the incoming order includes customized product fabrication data for each of the one or more customized products, customer information, and shipping information, and
wherein the incoming order is one of a plurality of incoming orders for customized products received from the customer;
determine, based on the customized fabrication data, an amount of fabrication time for each of the one or more customized products in the incoming order;
determine, based on the amount of fabrication time for each of the one or more customized products, an order shipment date for the incoming order;
in response to determining one or more predetermined linking criteria are met, the predetermined linking criteria including i) the order shipment date is within a predetermined number of days of a bundle shipment date for a shipment bundle containing one or more other orders of the plurality of incoming orders of the customer, and ii) a number of product vacancies in the shipment bundle is greater than a number of products in the incoming order, link, within a non-transitory data storage region, the incoming order to the shipment bundle, wherein
the shipment bundle is one of a plurality of shipment bundles, each shipment bundle including one or more orders of a plurality of orders for customized products placed by a plurality of customers, and
linking the incoming order to the shipment bundle includes assigning a bundle identification (ID) to the incoming order corresponding to the shipment bundle; and
after linking the incoming order to the shipment bundle and in response to determining that one or more predetermined shipping criteria are met, generate, for review by a user, a bundle shipment manifest for use in preparing the shipment bundle for shipping, wherein
the bundle shipment manifest is generated from a portion of the data associated with each of the customized products assigned to the bundle ID, and
the bundle shipment manifest lacks reference to the respective order of the plurality of incoming orders associated with each of the customized products.

18. A method for real-time processing and linking of a plurality of orders, comprising:
receiving, via a network from a computing system associated with a customer of a plurality of customers, an incoming order for fabricating one or more customized products,
wherein the incoming order includes customized product fabrication data for each of the one or more customized products, customer information, and shipping information, and
wherein the incoming order is one of a plurality of incoming orders for customized products received from the customer;
determining, by processing circuitry based on the customized fabrication data, an amount of fabrication time for each of the one or more customized products in the incoming order;
determining, by the processing circuitry based on the amount of fabrication time for each of the one or more customized products, an order shipment date for the incoming order;
in response to determining one or more predetermined linking criteria are met, the predetermined linking criteria including i) the order shipment date is within a predetermined number of days of a bundle shipment date for a shipment bundle containing one or more other orders of the plurality of incoming orders of the customer, and ii) a number of product vacancies in the shipment bundle is greater than a number of products in the incoming order, linking, by the processing circuitry within the non-transitory data storage region, the incoming order to the shipment bundle, wherein the shipment bundle is one of a plurality of shipment bundles, each shipment bundle including one or more orders of the plurality of orders, and linking the incoming order to the shipment bundle includes assigning a bundle identification (ID) to the incoming order corresponding to the shipment bundle; and after linking the incoming order to the shipment bundle and in response to determining that one or more shipping criteria are met, generating, by the processing circuitry for review by a user, a bundle shipment manifest for use in preparing the shipment bundle for shipping, wherein the bundle shipment manifest is generated from a portion of the data associated with each of the customized products assigned to the bundle ID, and the bundle shipment manifest lacks reference to the respective order of the plurality of incoming orders associated with each of the customized products.

19. The system of claim 1, wherein the one or more customized products are orthodontic aligners.

20. The system of claim 19, wherein the customized product fabrication data for each of the orthodontic aligners comprises dimensional specifications for the respective orthodontic aligner.

* * * * *